US007737327B2

(12) United States Patent
Falcone et al.

(10) Patent No.: US 7,737,327 B2
(45) Date of Patent: Jun. 15, 2010

(54) METHODS FOR SCREENING FOR GENES AND SMALL MOLECULES THAT ACTIVATE MAMMALIAN RECEPTOR PROTEINS

(75) Inventors: Deane Louis Falcone, Lexington, KY (US); John M. Littleton, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 566 days.

(21) Appl. No.: 10/795,455

(22) Filed: Mar. 9, 2004

(65) Prior Publication Data

US 2005/0204428 A1  Sep. 15, 2005

(51) Int. Cl.
*C12N 15/82* (2006.01)
*C12N 15/84* (2006.01)
*C12N 15/10* (2006.01)
*C12N 15/12* (2006.01)
*C12N 15/38* (2006.01)
*C12N 15/62* (2006.01)

(52) U.S. Cl. .................. 800/288; 800/282; 800/294; 800/306; 800/317.3; 435/6; 435/7.1; 435/8; 435/69.7; 435/421; 435/430.1; 435/468; 435/469

(58) Field of Classification Search .................. None
See application file for complete search history.

(56) References Cited

U.S. PATENT DOCUMENTS 6,989,236 B1 * 1/2006 Falcone et al. ............... 435/7.1
2003/0092057 A1 * 5/2003 Blume ......................... 435/7.1
2003/0211455 A1  11/2003 Tran et al.

FOREIGN PATENT DOCUMENTS

WO  WO 01/34821 A2  5/2001

OTHER PUBLICATIONS

Huang et al. Basic & Clinical Pharmacology & Toxicology 96: 3-14 (2005).*
Bays et al. Expert Opin. Pharmacother. 4(11): 1901-1938 (Nov. 2003)—Abstract Only.*
Guha et al. J. Hepatobiliary Pancreat. Surg. 8(1): 51-57 (2001)—Abstract Only.*
Agarwal, M. FEBS Letters 322(3): 207-210 (May 1993)—Abstract Only.*
Sevenet, T. J. Ethnopharmacol. 32(1-3): 83-90 (Apr. 1991)—Abstract Only.*
Hamilton, J. Prog. Lipid Res. 43(3): 177-199 (May 2004)—Abstract Only.*
Brinck et al. Acta Anat. (Basel) 161(1-4) 219-233 (1998)—Abstract Only.*
Cao et al. J. Nat. Prod. 69(4): 707-709 (Apr. 2006)—Abstract Only.*
DeBosscher et al. PNAS (USA) 102(44): 15827-15832 (Nov. 2005)—Abstract Only.*
Wess et al. Angew. Chem. Int. Ed. 40(18): 3341-3350 (2001).*
Rogers et al. PharmaGenomics 14: 27-28, 30 and 32-34 (Jul./Aug. 2003).*
Tanksley et al. Trends in Genetics 11(2): 63-68 (Feb. 1995).*
Srinivasan et al. The Journal of Biological Chemistry 274(38): 26633-26638 (Sep. 1999).*
Sadee et al. AAPS PharmSci. 3(3): online article 22, pp. 1-27 (2001).*
Broun et al. Science 282: 1315-1317 (Nov. 1998).*
Kim et al. Plant Molecular Biology 24(1): 105-117 (1994).*
Lloyd et al. Science 266: 436-439 (Oct. 1994).*
Drysdale et al. PNAS (USA) 97(19): 10483-10488 (Sep. 2000).*
Schena et al. PNAS (USA) 88(23): 10421-10425 (Dec. 1991).*
Wallace et al. pp. 279-305 In: High Throughput Screening, Devlin, J., ed., Marcel Dekker, Inc.: New York (1997).*
Littleton et al. Life Sciences 78: 467-475 (2005).*
Aoyama et al., "A glucocorticoid-mediated transcriptional induction system in transgenic plants", *The Plant Journal*, Blackwell Scientific Publications, Oxford, GB, vol. 11, No. 3, Mar. 1997, pp. 605-612, XP002082422.
Ouwerkerk et al., "Glucocrticoid-inducible gene expression in rice", Planta, Springer Verlag, DE, vol. 213, No. 3, Jul. 2001, pp. 370-378, XP002308212.
Zuo et al., "An estrogen receptor-based transactivator XVE mediates hightly inducible gene expression in transgenic plants", *The Plant Journal*, Blackwell Scientific Publications, Oxford, GB, vol. 24, No. 3, Oct. 2000, pp. 265-273, XP000990719.
Borevitz, et al., "Activation Tagging Identifies a Conserved MYB Regulator of Phnylpropanoid Biosynthesis" Plant Cell, merican Society of Plant Physiologists, Rockville, MD, vol. 12, No. 12, Dec. 2000, pp. 2383-2393, XP 002327891.
Van Der Fits, et al., "T-DNA activation tagging as a tool to isolate regulators of a metabolic pathway from a genetically non-tractable plant species", Transgenic Researcg, vol. 10, No. 6, Dec. 2001, pp. 513-521, XP002327891.
Littleton et al., "Rediscovering plant-based drugs", Nature Biotechnology, vol. 21, No. 8, Aug. 2003, pp. 843-884, XP002327871.

* cited by examiner

*Primary Examiner*—David T Fox
(74) *Attorney, Agent, or Firm*—McDermott Will & Emery LLP (57) ABSTRACT

Methods for screening mutations that affect the synthesis of plant small molecules or compounds capable of activating a mammalian nuclear receptor protein and systems for rapidly assigning functionality to genes that regulate plant secondary metabolism are provided.

14 Claims, 3 Drawing Sheets

METHODS FOR SCREENING FOR GENES AND SMALL MOLECULES THAT ACTIVATE MAMMALIAN RECEPTOR PROTEINS

FIELD OF THE INVENTION

The invention relates to methods for screening mutations that affect the synthesis of plant small molecules or compounds capable of activating a mammalian nuclear receptor protein. More particularly, the invention relates to the use of transgenic plants encoding a mammalian receptor whose activation is linked to a gene encoding a visible reporter gene to identify genes encoding small molecules or compounds that activate the receptor.

BACKGROUND OF THE INVENTION

Plants produce many small molecules with specific and potent biological activity. These are commonly economically important, either because they are valuable commercial products, or because they have regulatory functions as plant hormones or intracellular messengers. The genetic regulation of the synthesis of such compounds is often unknown. For example only a small fraction of the *Arabidopsis* genome is recognized as being involved in plant secondary metabolism. The problems in elucidating these pathways include low accumulation levels, transient or tissue-specific expression, or the complications associated with long multi-step pathways. To overcome these problems a strategy has been devised combining activation tagging mutagenesis (ATM) with pharmacological high throughput screening (HTS). In this, ATM of *Nicotiana tabacum* protoplasts are used to produce a mutant population of microcallus cultures, and individual clones that over-accumulate products with a specific biological activity are then selected after HTS. These mutant clones are then used to isolate the tagged genes responsible for this accumulation. This enables product-relevant genes to be identified without the requirement for understanding the metabolic pathway. However, because of the random nature of ATM, and the large genome size, as many as 300,000 individual mutants would need to be screened to cover the entire genome. Thus, there is a need for systems and methods to significantly increase screening throughput.

SUMMARY OF THE INVENTION

In one aspect of the invention there is provided a method for screening mutations that affect the synthesis of plant small molecules or compounds capable of activating a mammalian nuclear receptor proteins comprising (1) transforming a plant with a vector comprising a constitutive promoter operably linked to the mammalian nuclear receptor ligand binding domain which is operably linked to a transcription factor DNA binding domain and a transactivating transcriptional activator domain; and a gene encoding a visible marker operably linked to a transcription activator sequence and a promoter, to obtain a transgenic plant;

(2) isolating protoplasts from the transgenic plant;

(3) mutagenizing the protoplasts to form mutagenized protoplasts;

(4) culturing the mutagenized protoplasts into microcalli; and (5) selecting microcalli that overexpress the visible marker gene.

In another aspect of the invention there is provided a transgenic plant or plant tissue comprising a vector comprising a constitutive promoter operably linked to the mammalian nuclear receptor ligand binding domain which is operably linked to a transcription factor DNA binding domain and a transactivating transcriptional activator domain; and a gene encoding a visible marker operably linked to a transcription activator sequence and a promoter, wherein the transgenic plant or plant tissue overexpresses the visible marker.

In another aspect of the invention there is provided a plant cell line derived from the transgenic plant or plant tissue of the invention.

BRIEF DESCRIPTION OF THE DRAWINGS

FIG. 1 is a schematic drawing illustrating the elements of the nuclear receptor protein (NRP) inducible system. T-DNA is delineated by the right and left borders, labeled RB and LB in boxes at either end of the element. Block arrows within the element represent promoter sequences 35S from Cauliflower mosaic virus; NOS, nopaline synthase promoter; 6X UAS, six tandem repeats of the yeast GAL4 upstream activator sequence followed by −46 to +1 region of the 35S promoter (encompassing the TATA box sequence). $E9_T$, polyadenylation addition sequence of the pea ribulose bisphosphate carboxylase small subunit gene E9; $NOS_T$, nopaline synthase poly(A) terminator sequence; $3A_T$, poly(A) addition sequence of the pea rbc S3A gene. GVG, gene encoding the trimeric glucocorticoid-inducible transcription factor. The yeast GAL4 protein is at the N-terminus, the transactivating domain from herpes simplex virus VP16 protein, and the hormone binding domain of the rat glucocorticoid receptor is at the C-terminus.

FIGS. 3A-3D provide an example of GFP fluorescence from induced single protoplasts derived from glucocorticoid NRP transgenic tobacco. Two-day-old cells were induced for 20 hours with 10 microMol dexamethasone before photography. A. Protoplasts at 40× magnification. B. and C. 100× magnification. D. Photograph of elongating cells in same dish taken three days later at 100×. All green color is due to GFP fluorescence. Chloroplasts are evident as small red dots as chlorophyll autofluoresces under blue wavelength light. Yellowish spots in some cells are nuclei that are actually fluorescing intensely green but appear yellow from the lengthened exposure times used to enable the green fluorescence in the cytoplasm to be captured on film. Although not shown, non-induced wild type cells display only red autofluorescence and no green coloration.

DETAILED DESCRIPTION OF THE INVENTION

This invention provides methods and systems for significantly increasing screening throughput of mutants by using the plant cell itself to screen for biological activity. To this end, transgenic lines of *N. tabacum* and *Arabidopsis* have been engineered to express nuclear receptor proteins (NRPs) that are linked to the expression of a visible marker protein, e.g., green fluorescent protein (GFP) or luciferase. Cells from this line exposed to activators of the NRP are identifiable by visible screening, for example, under a fluorescence microscope for the accumulation of GFP. These transgenic lines are used to produce a population of mutant protoplasts by ATM, and individual cells that over-accumulate relevant products are identified by marker protein, e.g., GFP expression. Each "positive" cell line may be used to identify the type of compound responsible for the biological activity, and for recovery of genomic DNA adjacent to the activation T-DNA tag (plasmid rescue, genomic walking). Candidate sequences are evaluated for their ability to reproduce the marker-positive phenotype, e.g., GFP-positive when inserted into protoplasts, and may be sequenced by high throughput DNA sequencing. Overexpression of the positive genetic material is evaluated in whole plants to establish its metabolic impact at this level. In particular, the focus is on products with biological activity at mammalian nuclear receptor proteins, such as corticosteroid NRP, Liver X receptor, estrogen NRP, glucocorticoid, mineralcorticoid, androgen, progesterone group, farnesoid X receptor, vitamin D receptor, and peroxisome proliferator-activated receptor (PPAR). These NRPs are known to respond to specific sterol products of plant secondary metabolism, and have known sequences and pharmacological profiles. However, the systems and methods described herein are adaptable and applicable to many small molecule plant metabolites with biological activity. Although many of the genes identified by this strategy may have only indirect effects on the pathways leading to the biologically active products, their characterization will help elucidate regulation of secondary metabolism. Similarly, characterization of the T-DNA and flanking sequences will provide new information regarding gene structure and organization.

The methods and systems provided by this invention aim to functionally identify a broad range of genes that influence the production of plant metabolites. The genes identified by these methods are uncovered in a forward fashion, that is, the effect of the overexpressed genes on the production of metabolites, including secondary metabolites, in plant cells is observed. Upregulated expression of genes as a result of the mutagenesis step employed in the methods leads to an increased synthesis of a class of plant metabolites. Consequently, an important functional characteristic of the tagged genes is provided immediately. Specifically, overexpression of the identified gene leads to increased production of the small-molecule activity (in comparison to production of activity detected in a wild-type plant). While the total number of plant genes that influences the synthesis of compounds in this way may not be large, this approach will result in the identification of any gene which exerts this effect. Thus the primary identification of each tagged gene is determined on this functional basis.

The types of genes that may be identified using the genetics-based methods of the invention are conceivably broad. Because any gene whose overexpression leads to pathway upregulation can be isolated, genes encoding products that function as pathway regulators, in signaling, or as pathway-specific enzymes are possible candidates. Many features of plant secondary metabolism make this one of the most significant aspects of this strategy. The biosynthetic pathways that lead to the production of secondary compounds are highly diverse and complex, often requiring a large number of enzymatic steps and multiple regulatory layers. For thoroughly studied pathways, it is now well documented that developmental, temporal and tissue-level control are common regulatory mechanisms for such natural product pathways. All of these forms of regulation are evident from research conducted on a variety of plant specific pathways. One example is the biosynthesis of terpenoids (McGarvey and Croteau 1995), which includes a vast assortment of aromatics and, in many species including *Mentha,* accumulate in glandular trichomes at specific developmental stages and times. All of the enzymes required for the synthesis of these *Mentha*-specific terpenoids are expressed exclusively in glandular cells with the primary mechanism of regulation occurring at the transcriptional level (Lange et al. 2000, Proc. Natl. Acad. Sci USA, 97:2934-9; McCaskill and Croteau 1995, Planta, 197:49-56).

The present methods and systems allow for screening of extremely high numbers of cells harboring distinct activation mutations. Considering the genome size of plants, such as *Nicotiana tabacum* and *Arabidopsis,* which are particularly well suited for such studies, such high throughput screening capacity is essential. The experimental strategy transforms the desired phenotype, that of elevated accumulation of plant-derived molecules, to a visible response sufficiently sensitive to permit detection at an individual cell stage. A functional approach is thus applied in two respects, that of the biological activity of the plant molecule itself and of the genes that exert this upregulation. This approach yields distinct, new resources and information. It also makes available a mutagenized population of plant tissue and whole plants that can be studied further, and it will provide the genomic data concerning the overexpressed genes that lead to the increased biological activity. Also, because the plant sequences are isolated as genomic clones associated with a T-DNA tag, additional genomic sequence information will be obtained. Details regarding gene redundancy, density and organization will also be elucidated. The derived sequences of a particular plant in which the studies are conducted will be informative for comparative analyses to other plant genomes such as *Arabidopsis,* rice and maize. Finally, the influence of each mutation on the physiology of whole plants can be observed, once plant tissue is regenerated from screen-positive calli.

An additional outcome of the high throughput screening methods and systems provided herein is that an inventory of sequences that influence specific small molecule synthesis will be made available. Such a collection of genes will help to address questions relating to how pathways that lead to small molecule synthesis are signaled. In a handful of pathways well elucidated at the biochemical and genetic levels, metabolite accumulation in response to an inductive signal has been shown to be the consequence of upregulation of both the immediate biosynthetic pathway as well as the preceding, "supply" pathways. This coordinated expression among the requisite, distinct pathways involved in the synthesis of a given plant metabolite is probably common. For example, the tryptophan pathway supplies precursors for subsequent, secondary pathways and a study of its regulation provides experimental support for this phenomenon. Genes encoding enzymes of the tryptophan pathway were found to be upregulated in concert to meet the increased demands for synthesis of the secondary metabolite camalexin, an indolic phytoalexin, derived from tryptophan (Zhao and Last 1996, Plant Cell, 8:2235-2244). This finding demonstrated that distinct primary and secondary pathways are interlinked and co-regulated to respond to the requirements for synthesis of a secondary metabolite. A mechanistic explanation for whole-pathway coordination is suggested by the recent discovery of a transcriptional regulator, ATR1, which has been shown to control expression for the first step in the tryptophan pathway (Bender and Fink 1998, Proc. Natl. Acad. Sci. USA, 95:5655-5560). This Myb-like transcription factor positively regulates expression of anthranilate synthase and perhaps additional genes within the tryptophan and related secondary pathways.

The increased production of flavonoids in response to irradiation with ultraviolet light provides another example for multiple pathway regulation. Genes within the primary shikimate pathway and the secondary flavonoid pathway were found to be selectively coinduced, reflecting an integrated response to enable rapid metabolite accumulation without depleting intermediates from the respective pathways (Logemann et al. 2000, Proc. Natl. Acad. Sci. USA, 97:1903-1907). Thus an emerging view is that supply, generally primary, pathways are appropriately coordinated to maintain homeostasis when products or precursors from them are channeled into the production of new metabolites (Yao et al. 1995,Plant Cell, 7:1787-1799).

Another example of how a single gene regulator mediates changes in small molecule metabolism was provided by the isolation of the transcription factor, ORCA3, from *Catharanthus roseus*. Overexpression of this regulator results in the overexpression of a number of metabolite biosynthetic genes from more than one pathway and in turn results in the accumulation of terpenoid indole alkaloid products. The Orca3 regulator also has a role in signaling as it provides for a mechanism that links small-molecule synthesis to cellular stresses indicated by the level of jasmonic acid. Finally, and of relevance to the mutagenic approach to be used here, the ORCA3 gene was isolated by activation T-DNA tagging in a positive selection procedure, again demonstrating that pathway regulators are possible gene candidates with this type of mutagenesis.

The basic method for activation mutagenesis has been known for several years (Fritze and Walden 1995, Meth. Mol. Biol., 44:281-294; Fritze et al. 1995, Plant J., 7:261-271; Walden et al. 1995, Meth. Cell Biol., 49:455-469, each incorporated herein by reference). In this technique, enhancer sequences from the Cauliflower mosaic virus 35S promoter are incorporated (via *Agrobacterium* mediated T-DNA transfer) at random into the plant genome, and produce activation of genes in the immediate vicinity of the incorporated DNA. Because the enhancers cause deregulation of promoters nearby, gene overexpression generally results, usually conferring a dominant, gain-of-function mutation that is immediately scorable, making this mutagenesis technique ideally suited for conducting screens at the callus or individual cell level. Activation of promoters has been found to occur up to 3.6-kb from the T-DNA insert in *Arabidopsis* and the enhancers function independent of orientation, leading to gene overexpression either upstream or downstream from the T-DNA integration site (Weigel et al. 2000). In addition, because the relevant locus is "tagged" with the inserted T-DNA element, a variety of techniques exist to enable the straightforward recovery of the associated genomic DNA, including plasmid rescue, probably one of the most efficient genomic cloning techniques available. This very powerful mutagenesis technique has been applied most successfully using positive genetic selection procedures, such as survival of cells or tissue in the presence of specific inhibitors for essential enzymes (Fritze et al. 1995), in the absence of required growth factors (Kakimoto 1996, Science, 274:982-5) or under restrictive growth conditions (Furini et al. 1997, EMBO J., 16:3599-608). Recently, whole plant screens conducted primarily with *Arabidopsis* have resulted in the isolation of a number of genes involving developmental processes or other mutations conferring visible phenotypes (Borevitz et al. 2000, Plant Cell, 12:2383-2394; Huang et al. 2001, Plant Physiol., 125:573-584; Kardailsky et al. 1999, Science, 286: 1962-5; Weigel et al. 2000, Plant Physiol., 122:1003-13). Thus activation T-DNA tagging has proved effective for the isolation of a wide range of different genes in several different plant species. However, the use of it to create mutations that lead to the accumulation of active metabolites that confer no visible phenotype previously has not been accomplished.

The present activity-based screen is conducted at the level of microcallus tissue, which is derived from protoplasts mutagenized by T-DNA gene activation. The primary steps of the screen are generally to nondestructively sample mutagenized callus tissue, prepare a crude extract from this tissue sample and conduct assays for small-molecule activity. The essential property for small molecules of interest is that they bind to a mammalian receptor of interest, such as the glucocorticoid receptor, estrogen receptor, androgen receptor, progesterone receptor, mineralocorticoid receptor, liver X receptor, for example, present in the plant. For these purposes, (identifying cultures that overproduce such compounds) it does not matter whether the binding activity results in activation (agonists) or inhibition (antagonists) of receptor function. Thus the simplest way of testing for such compounds is by a radioligand displacement assay (Gattu et al. 1995, J. Neurosci. Meth., 63:121-125; incorporated herein by reference). In this method, a compound that binds with a very high affinity and selectivity to the desired NRP is radiolabeled and allowed to equilibrate with a membrane fraction containing the NRP. When unlabelled compounds that also bind to the NRP are present there is competition for the binding sites between these and the labeled ligand. As a result, less radiolabel will associate with the membranes.

Other processes that may be used in the present invention include methodologies to propagate, array and sample the mutated plant, e.g., callus tissue derived from individual protoplasts. Mutated cells are prepared by transformation of freshly isolated leaf protoplasts by co-cultivation with *Agrobacterium* harboring the activation-tagging T-DNA element. After this co-cultivation step, protoplasts are washed and embedded within a low-gelling temperature agarose to allow development of the transformed protoplast cells, now under antibiotic selection for the T-DNA, into microcalli. This generates the primary, mutated tissue in an agarose-embedded format in 60-mm petri dishes. Typically, 10 to 14 dishes per bimonthly experiment are generated, although the total number of transformants per dish, which represents an individual co-cultivation event, in practice is highly variable.

At this stage, the microcallus tissue can be "disembedded," diluted and surface plated. Once in this form, growth of the diluted microcalli, embedded onto the surface of agar-solidified media, is allowed to proceed until the material is large enough to sample. Sampling of the individual, mutated microcalli, now grown to a diameter of about 0.5 cm, is conducted by removing a small portion of tissue, for example, with a pair of ring forceps. The tissue sections may be placed into wells of 48-well microtiter plates where approximately one-half of each sample is used to prepare crude aqueous extracts for displacement assays and the remaining portions retained in the wells of the plate. Because the sampling and extraction steps are conducted under sterile conditions and in callus growth media, essentially all of the retained material can re-grow in the 48-well dishes, and in this way a "master" mutant tissue library is established. Extracts are prepared, for example, by macerating the excised tissue portion in a microcentrifuge tube with a micropestle attached to a low speed drill, pelleting the debris by centrifugation at 13,000×g for ten minutes and transferring the resulting supernatant to fresh tubes. Volumes are precisely set to obtain 700 μL of the supernatant, for example, to provide 200-μL samples for displacement assays in triplicate.

The basic technology that makes this approach possible is the use of mammalian nuclear receptor proteins (NRP) in plant cells. These are members of the nuclear steroid hormone receptor group, which include the glucocorticoid (GR), mineralocorticoid, estrogen (ER), androgen, and progesterone receptors. After becoming activated by binding specific hormone molecules in the cytoplasm, the receptor-ligand complex moves into the nucleus and activates transcription of target genes.

If very few lines are obtained from the screen that show constitutive marker expression, e.g., GFP fluorescence, after one or two rounds of tagging mutagenesis, it is possible to alter the sensitivity of the NRP response (Abe et al., 2001, Biochem. Biophys. Res. Commun., 281:122-125). For example, it was shown that some polyphenolics, including gallocatechins such as (−)-epigallocatechin-3-O-gallate, can enhance the activity of a mouse mammary tumor virus promoter, which is also responsive to glucocorticoid induction. This effect was only seen when a low level of inducer (200 nm dexamethasone) was present simultaneously (Abe et al. 2001). Thus, sub-induction levels (i.e., transcriptionally induced but below the detection limit for visualization of GFP fluorescence) using dexamethasone or other NRP inducers such as (−)-epigallocatechin-3-O-gallate, gallate, catechin, and other phenolics can be achieved. For example, the minimum concentration of dexamethasone required for visible induction of the glucocorticoid receptor is about 0.1 µM.

Nuclear receptors play important roles in human physiological processes by acting as sensors to transduce chemical signals to changes in gene expression. Their widespread involvement in diverse areas of metabolism, including many pathological conditions, make nuclear receptors key therapeutic targets for the development of new drugs.

Forty-nine distinct nuclear receptors are encoded in the human genome. This represents a large set of ligand binding domains that could be employed as specific targets for the discovery of new biologically active compounds. Included among these are nuclear receptors categorized as classic endocrine receptors mediate the action of many steroid hormones. This group includes the glucocorticoid, mineralcorticoid, estrogen, androgen, and progesterone receptors. A second nuclear receptor class responds to dietary lipids. Members of this category include the peroxisome proliferator-activated receptor (PPAR), which respond to various fatty acids and is implicated in cellular energy metabolism. Other potentially useful mammalian receptors for in situ based plant drug discovery include, the liver X receptor, which functions in the regulation of lipid and cholesterol metabolism, the farnesoid X receptor, involved bile acid/cholesterol homeostasis, and the vitamin D receptor.

Illustrating the importance of plants as sources of new natural products that function as distinct ligands for such receptors is the recent finding that guggelsterone, a compound from the Guggul tree, is an antagonist of the farnesoid X receptor. When supplied to mice reared on a high-cholesterol diet, guggelsterone was found to decrease hepatic cholesterol. This result underscores an important premise of the in situ detection strategy, which is that a variety of additional, unknown natural ligands exist for nuclear receptors and that these may exhibit useful therapeutic potential.

EXAMPLES

Example 1

Production of Transgenic NRP-GFP Reporter Lines

Figure 1:
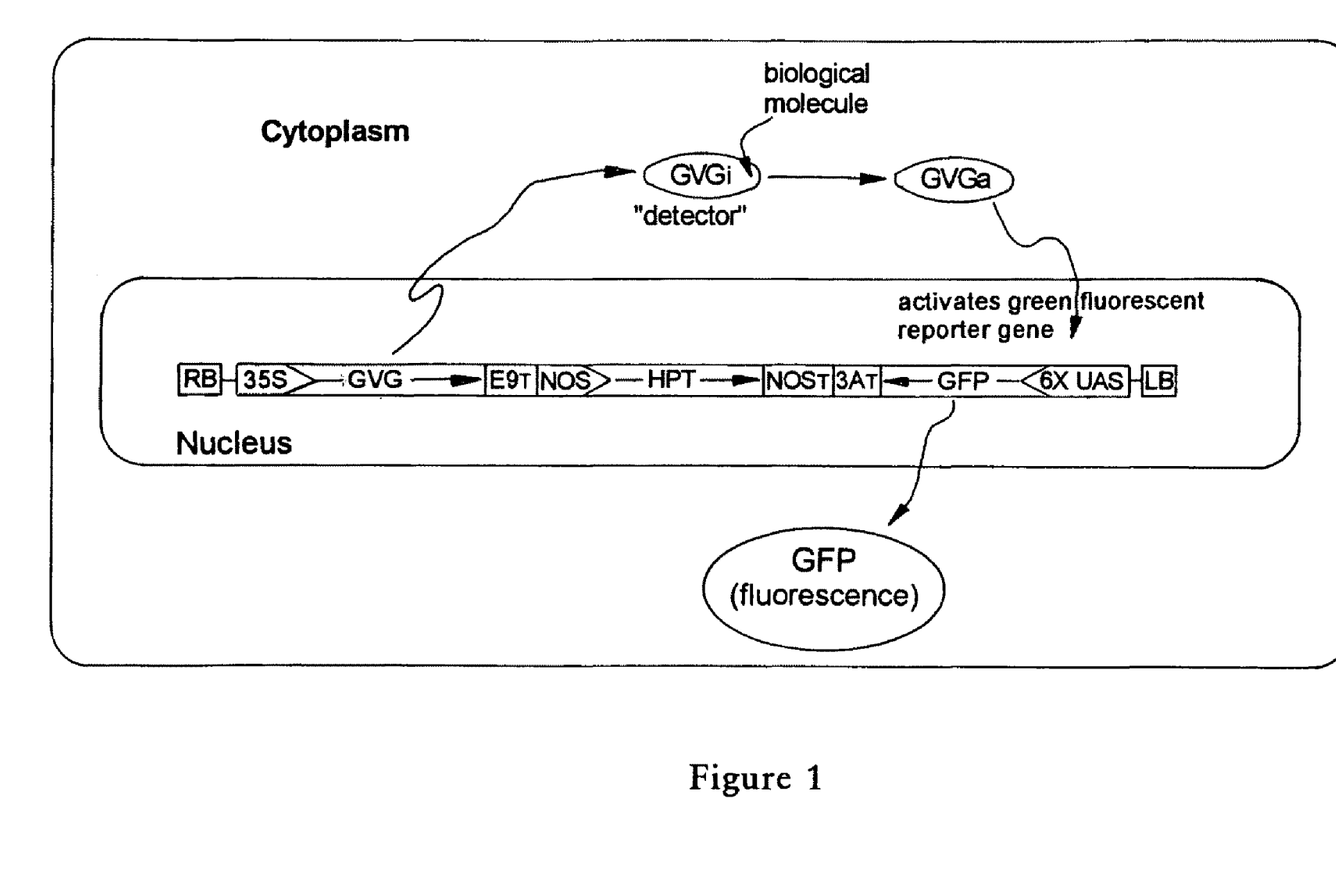
Figure 2:
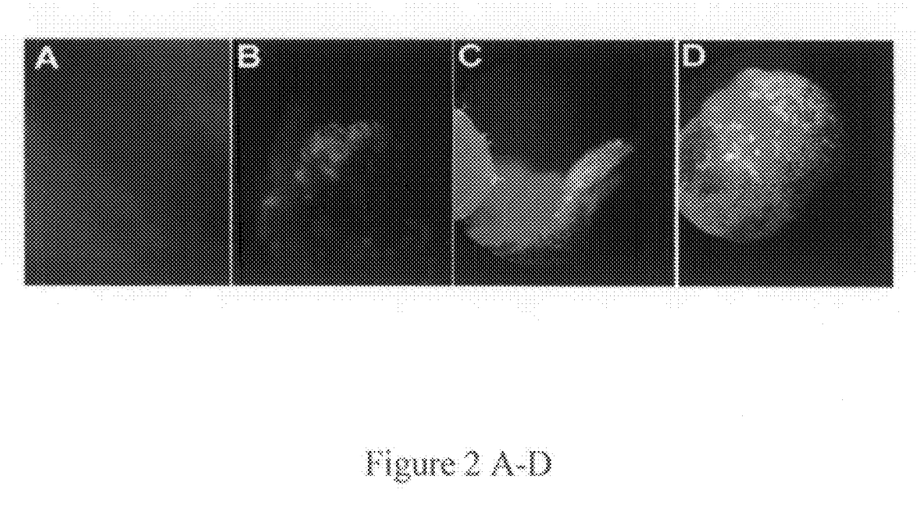
FIG. 2A-D are photographs of the upper parts of leaves of an *Arabidopsis* transgenic line after treating the seedlings with the indicated concentration of various inducers. Seedlings were exposed for 48 hours before viewing under blue (470 nm) wavelength light at 40× magnification. A. Control. Leaf surface with no inducer; or treated with 1 microMol dexamethasone (B); 30 microMol progesterone (C); or 30 microMole hydrocortisone.

Using the basic "GVG" glucocorticoid system developed by Aoyama, (Aoyama and Chua 1997, Plant J. 11:605-612), a construct using the GFP version, smGFP from Davis and Vierstra (Davis and Vierstra 1998, Plant Mol. Biol., 36:521-8) (FIG. 1), worked well at the whole-plant level as detected in seedlings treated with various corticosteroid and steroid inducers (FIG. 2). This indicated that a variety of inducers lead to a level of GFP expression that can be easily detected in various plant cells. The same construct expressed in tobacco however, failed to show any detectable GFP fluorescence whatsoever. After confirming strong transcriptional induction using dexamethasone in these transgenic tobacco plants using RT-PCR, different GFP versions that permit clear fluorescence detection in tobacco tissue were evaluated. An *Agrobacterium*-mediated leaf infiltration method was used to efficiently screen for the most intense fluorescing GFP derivative in tobacco tissue (Yang et al. 2000, Plant J. , 22:543-551). Separate constructs were made for each of three different GFP sequences. The original GFP version (Davis and Vierstra 1998) used and two modified versions were placed in front of a constitutive promoter (CaMV 35S) along with a translational enhancer (TE) sequence at the 5' end of each GFP coding region (von Arnim et al. 1998, Gene, 221:35-43). The approach involves the transfer of the 35S::TE::GFP constructs, within the T-DNA of a standard plant transformation vector, into plant cells following manual infiltration of the transformed *Agrobacteria* into the leaf intercellular space with a syringe plunger. *Nicotiana benthamiana,* a tobacco species on which this transient expression technique had been developed and optimized, was first used. Two GFP sequences, mGFP4 and mGFP5 (Siemering et al. 1996, Current Biology, 6:1653-1663), yielded detectable green fluorescence upon excitation with blue light but not with the construct harboring the GFP gene used originally. mGFP5 showed the most intense fluorescence on repeated experiments. This new version was then shown to be the only one detectable under blue fluorescent light in the tobacco species used for routine protoplast isolation and mutagenesis, *N. tabacum* SR1.

PEG-mediated DNA uptake was then used as a final transient expression test to determine if GFP fluorescence could be visualized at the level of single cells isolated from the SR1 line (Walden et al. 1994, Plant Mol. Biol., 26:1521-1528). Fluorescence microscopy of tobacco cells transfected with the mGFP5 version, along with transfected controls, indicated clear GFP fluorescence that was well above background.

Figure 3:
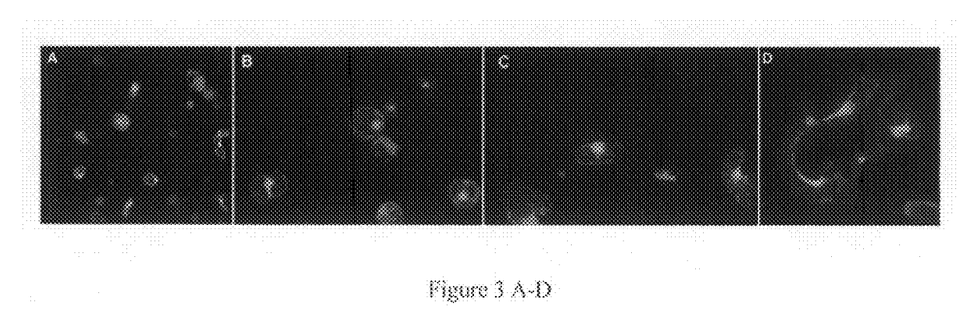

Stably transformed SR1 tobacco lines prepared with the glucocorticoid NRP constructs containing mGFP5 reporter genes were then generated. Shoots from independently transformed lines were examined for optimal GFP induction characteristics using shoot sections treated with 1 and 10 µM dexamethasone for 12 hours. Ten out of 60 independent lines showed very clear GFP fluorescence and were transferred to soil to obtain whole plants. Leaves from some of these lines were used for protoplast isolations to get an early indication of GFP induction at the single cell stage (FIG. 3). Six out of the ten of these were then analyzed at the seedling level and four lines displayed good induction in all progeny tested at the seedling level (using about 50 seeds) and two lines exhibited the most sensitive induction showing clear fluorescence after six hours with 1.0 µM dexamethasone.

Example 2

Design and Production of an Estrogen-NRP Reporter

There is a considerable amount of literature on the use of biosensors to detect biological compounds in the environment. One of the most relevant is the use of genetically engineered yeast cells as biosensors for the presence of environmental estrogens (Coldham et al. 1997, Environ.Health Perspect, 105:734-42) (these come from several sources including plants and pesticides). The principle is based on yeast transfected with a mammalian estrogen receptor (ER) and ER response element, and this is linked to a gene (the yeast URA3 gene) to create a positive selection system. In the presence of estrogen there is overexpression of the URA3 gene and yeast cells survive on synthetic media lacking uracil, a condition in which the background yeast strain (a uracil auxotroph) is unable to survive. The transfected yeast is thus used as a positive screen for the presence of exogenous estrogens. Since endogenous estrogens are not produced in yeast this is not a problem for the screen, but plants produce phytoestrogens and so the expression of this construct in plant cells could provide a means of selecting those cells that overproduce phytoestrogens. Because of this, and the fact that ligands, which show activity at glucocorticoid receptors may not be as prominent in plant cells, an estrogen-responsive system also utilizing a mammalian NRP that will function in the same way as the glucocorticoid-based induction system has been constructed. This approach provides a means to detect a greater range of plant molecules with ER binding activity and these include a range of plant polyphenolic molecules, including flavonoids.

The design of the estrogen NRP-based reporter element follows the basic format as that for the GR construct (FIG. 1) (Aoyama and Chua 1997). In this case, the human estrogen-receptor hormone binding domain (hER-HBD) that had been fused to GAL4-DNA binding domain and the VP16 transcriptional activation domain was obtained from D. Picard (Univ. of Geneva) (Louvion et al. 1993, Gene, 131:129-34). A PCR-based subcloning strategy was developed to place this element encoding the chimeric estrogen-inducible transcription factor (GAL4/hER-HBD/VP16) in front of the 35S promoter of CaMV, and to insert the gene encoding mGFP5 (Siemering et al. 1996) in front of the 35S minimal promoter-GAL4 upstream activation sequence (see FIG. 1 for conceptual layout). Testing and validation of this system was conducted as described for the GR-NRP, but using β-estradiol and other estrogens, including plant-derived compounds such as flavonoids, which are known to show stimulation of estrogen responsive element (ERE) promoters (Moosmann and Behl 1999, Proc. Natl. Acad. Sci. USA, 96:8867-72)

The system was validated by testing for the responsiveness (i.e., induction of GFP expression by detection of visible GFP fluorescence) of several classes of plant molecules.

Example 3

Production of a Large Population of Mutant Protoplasts from the NRP Transgenic *N. Tabacum* Lines by *Agrobacterium*-Mediated ATM This step includes the isolation of protoplasts from the transgenic lines that express the glucocorticoid receptor-GFP reporter system i.e., the NRP transgenic lines, and transformation of these cells by *Agrobacterium*-mediated T-DNA transfer, for mutagenesis. Leaf protoplasts are prepared by the general method as described (Walden et al. 1995, incorporated herein). Briefly, 4-5 week old MS media-grown (Murashige and Skoog 1962, Physiol. Plant, 15:473-497) transgenic tobacco lines harboring the NRP-GFP detection system are used as a source of leaf material for protoplast isolation. Leaf pieces from sterile-grown plants are digested by overnight incubation in a 1.5% cellulase-0.5% pectinase (Sigma) mixture in plant cell culture medium (K3 media) at 26° C. in the dark. Released protoplasts are recovered by sieving through a 105 μm mesh and purified by repeated low speed centrifugation (2000 rpm, in a swing-out rotor), conditions whereby intact, viable protoplasts float and nonviable cells and debris pellet. Protoplasts are incubated for further steps in culture dishes at $1\times10^6$ cells per 10 mL media.

Transformation with the activator T-DNA tag to mutagenize the plant cells is performed by co-cultivation with *Agrobacterium tumefaciens*, strain GV3101 (Koncz and Schell 1986, Mol. Gen. Genet., 204:383-396), harboring the plasmid pPCVICEn4HPT (provided by R. Walden), which contains the activation T-DNA tagging element (Fritze and Walden 1995, Meth. Mol. Biol., 44:281-94). Freshly grown bacterial cells are added directly to six to eight day-old protoplast cultures in a ratio of 100:1 bacteria to protoplast cells. Co-cultivation is conducted at 26° C. in the dark for 48 hours. At the end of the incubation period, protoplasts are washed three times in W5 media (154 mM NaCl, 125 mM $CaCl_2 \cdot 2H_2O$, 5 mM KCl, 5 mM glucose, pH 5.6-6.0) by centrifugation in a swing-out rotor at room temperature. Protoplasts are resuspended in 0.4 M sucrose K3 media to produce a final concentration of $1\times10^6$ protoplasts per mL. One mL of protoplast suspension is transferred to a standard (100 mm) petri dish and cultured in a final volume of 10 mL of 0.4 M sucrose K3 media containing antibiotic selection against *Agrobacterium* cells (cefotaxime 500 μg mL$^{-1}$) as well as the presence of hormones to maintain cells in a dedifferentiated state [auxin (naphthalene acetic acid, NAA) 1.0 μg mL$^{-1}$ and cytokinin (kinetin) 0.2 μg mL$^{-1}$]. Hygromycin (15 μg mL$^{-1}$) or kanamycin (20 μg mL$^{-1}$), depending on the selectable markers present on additional versions of the tagging element we have produced, is also added to the incubation media to select for the protoplasts transformed with the activation-tagging vector. Control transformations are also performed with vectors lacking the enhancer sequences, which provide a means to assess false positives in a given co-cultivation experiment.

Culturing of protoplasts into microcalli is continued by embedding the cells in 0.3% low-gelling temperature agarose (SeaPlaquee®, FMC Bioproducts, Rockland, Me.). K4 media, a new media we have adopted for subsequent microcallus culturing because of more vigorous growth at this stage, is then added to the petri dishes containing the soft agarose-embedded microcalli. This media also contains all hormones and selective antibiotics as noted above, but replaces the nitrate salts ($NH_4NO_3$ and $KNO_3$) used in the conventional K3 plant growth media with glutamine, asparagine and arginine (Fritze et al. 1995, Plant J., 7:261-271). Following protoplast embedding, the K4 media is reduced in osmolarity at 0.1 M increments, (starting at 0.4 M sucrose, ~580 mOsm) on a weekly basis by changing the liquid phase media over the soft agarose-embedded cells. Once microcalli are established (usually four to five weeks), they are released from the agarose by gentle maceration and dilution. Microcalli are further cultured by "surface plating" the transformed tissue to 0.1 M K4 media solidified with agarose in 150 mm dishes. Dilutions are made empirically to adjust the number of individual microcalli on each dish to densities sufficient to enable clear separation for microscopic screening and for continued growth of the microcalli up to the stage of sampling.

Example 4

Isolation of those Cells (or Microcalli) over-expressing GFP by Micro-Manipulation under Fluorescence Microscopy Screening for the presence of elevated plant metabolites by fluorescence microscopy can occur soon after embedding microcalli in agarose. The sizes of the microcalli at this stage are usually highly variable. Because of this it is advisable to adjust the density during embedding as indicated above to enable the clear visualization of smaller microcalli that might be obscured by larger calli. Visualization of GFP fluorescence is conducted by placing the petri dishes in which the microcalli is embedded directly on the stage of a Nikon Eclipse TE 200 inverted microscope, equipped with a super high pressure mercury vapor lamp and power supply and fitted with filter blocks for GFP excitation and emission (excitation wavelengths: 470-490 nm; emission wavelengths: 520 nm and above). Excitation and the resulting fluorescing illumination pass directly through the polystyrene lids of the dishes, enabling screening to be conducted without having to open them and exposing the tissue to non-sterile conditions. Any fluorescing microcalli are marked on the dish and monitored for fluorescence regularly as they develop. Controls always include transgenic tissue at the same stage to which various concentrations (0.1, 1.0 µM) of inducers, generally dexamethasone, will be added. Microcalli that exhibit stable, continuous fluorescence under blue-wavelength light at later stages of growth are considered positives for the primary screen and are isolated by manual transfer when the material has grown to appropriate sizes. No fluorescence has been detected in the absence of exogenously applied chemical inducers. Thus we expect a low level of background false positives for the corticosteriod receptor screen.

Example 5

Establishment of Cells as Mutant Lines

The activation-tagged plant cells identified from the primary screen on the surface of agar-solidified media are further grown to obtain distinct "macrocalli" for sampling and extract preparation. Continuous monitoring for GFP fluorescence is conducted microscopically as the callus tissue develops. Sampling is initiated when the surface-plated callus material attains a size of approximately 0.5 to 1.0 cm in diameter. Individual calli are sampled by excising approximately 50 mg from the callus and performing a "partial" maceration of this tissue in wells of a 48-well microtiter plate. The partial maceration is performed in fresh growth media, enabling a small proportion of cells from the callus to remain intact and viable. The supernatant extract resulting from this tissue maceration is removed to complete the extraction and then centrifuged to remove debris. Liquid growth media is added to each of the 48 wells in the plate to replace this and these are further incubated to allow for recovery of the remaining intact cells. Because all of these steps are conducted under sterile conditions, the partially disrupted calli are able to grow, and this in effect establishes the "master" library by which the viable mutagenized material can be maintained for several months. Since displacement activity data from the pharmacological screen is usually obtained within one to two weeks of sampling, the material, arrayed in the 48-well microtiter plates, can be used to recover any confirmed positives. Thus, by this means, sampling, extract preparation and establishment of a viable library of the mutagenized population is conducted in a single step. Throughout the recovery process, as the mutated calli are continuously monitored as noted, positive mutants are confirmed by detecting GFP fluorescence in microcalli that has redoubled their mass on the surface of agar-solidified media after being divided into small pieces.

Example 6

Use of Extracts of Mutant Microcalli to Confirm Increased NRP Biological Activity in a Conventional Pharmacological Radioligand Binding Screen GFP-positive tobacco cells derived from the primary screens are arrayed as microcalli in 48-well microtiter culture dishes. Lines grown in this format can be maintained for periods of four to six months without the need for further transfers or additional manipulations. Thus the culture library provides a master set of mutated material during which the secondary analysis is conducted. The callus library also serves to continually propagate the mutated material as undifferentiated tissue as a contingency in the event that regeneration of any positive callus clones to whole plants is not possible or efficient. In such cases, it is possible to isolate genomic DNA from callus tissue for Southern analysis and gene cloning procedures.

The secondary screen consists of pharmacological assays conducted on extracts prepared from callus tissue in the master library. A glucocorticoid receptor binding assay is used to test extracts of cultures for production of GR ligands. The methods for radioligand binding to the glucocorticoid receptor are modified from described generalized procedures (Kam et al. 1993, J. Immunol., 151:3460-66; Soldin et al. 1992, Ther. Drug Monit., 14:164-68, both incorporated herein by reference). Radioligand binding is performed to confirm correlation between ligand binding and reporter activity, as well as to assess the presence of endogenous glucocorticoids in transgenic cultures.

Mammalian steroid receptors are prepared by homogenizing 1 g of finely minced rat liver tissue in a solution containing 0.32 mM sucrose, 0.02 mM Tricine, 2mM $CaCl_2$, and 1 mM $MgCl_2$ (pH 7.4), in a hand-held glass homogenizer and applying approximately 30 strokes with a Teflon pestle. The homogenate is centrifuged at 100,000×g at 4° C. for one hour and the supernatant, containing the cytosolic fraction, is retained. Protein concentrations are measured using a commercial kit based upon a modified Lowry method (Sigma, St Louis, Mo.).

The radiolabeled glucocorticoid ligand is prepared from stock solutions of [$^3$H]-dexamethasone (Amersham, Arlington Heights, Ill.) by addition to 1 mL of 95% ethanol and 9 mL 0.32 mM sucrose. This working stock solution is then diluted for a final (per well) concentration of 10 nM. The radioligand-binding assay is conducted by adding unlabeled and radiolabeled glucocorticoids in ethanol to 10 mL polypropylene tubes and evaporating under nitrogen gas. 500 µL aliquots of the glucocorticoid receptor preparation are added to each tube, and the tubes are incubated for three hours at room temperature. Extracts prepared from individual microcalli displaying stable GFP fluorescence are used in competition binding experiments to determine if glucocorticoid small-molecule activity is elevated. All experiments are run in duplicate determinations. The binding reaction is terminated by the addition of 5 mL of ice-cold, 5 mM HEPES buffer containing 0.2 mM EDTA (pH 7.4) and the tube contents are filtered through a nitrocellulose filter. Data are collected as counts per minute (CPM) with a Packard Tricarb 2100TR liquid scintillation vial counter. Specific binding is defined as total binding minus non-specific binding, (the latter is determined in the presence of 10 µM cold dexamethasone). Data are presented as the mean of pooled replicates ±SE. Group means are compared by analysis of variance and multiple range testing. Quantification of the specific binding activity is done, for example, by comparisons to standard curves generated by plotting the CPM of [$^3$H]-dexamethasone standards versus the concentration of dexamethasone (µg L$^{-1}$). An activity table of steroid standards (hydrocortisone, prednisone, betamethasone, triamcinolone, and β-estradiol as a negative control) will then be generated, expressing activity as units of dexamethasone activity equivalents. Concentrations of unknown samples are then estimated based on "dexamethasone equivalents". Non-specific binding is determined as previously described (expected to be approximately 10%) and from callus extracts cleared of polyphenolics as well as glucocorticoids. These glucocorticoid-free extracts are prepared from plant cell culture extracts by centrifugation at 5000×g for five minutes to remove any cellular debris, and mixing the resulting supernatant (1 mL) with 100 mg activated charcoal. After incubation at room temperature for two hours, the charcoal is removed by washing 2× with centrifugation at 40,000×g for 20 minutes. This methodology is a variation of a wide-ranging number of methodologies utilized clinically to estimate blood steroid levels of patients undergoing steroid therapy.

Any GFP-positive lines that show elevated activity in the specific pharmacological binding assays are followed up by GC/MS analysis of cultures overproducing GR ligands. The "surface-plating" regime developed during the microcallus screen for alkaloidal activity, are applied to individual callus clones to amass tissue for extractions. The exclusive use of surface-grown material at these stages (as opposed to bulking up material by liquid culture growth) provides a means to minimize secondary, somatic cell mutations that are possible if the plant tissue is maintained as rapidly growing undifferentiated cultures for prolonged periods (Phillips et al. 1994).

Surface-grown callus tissue from individual lines are used for preparing concentrated extracts for GC analysis. Using described methods (Bruni et al. 2001), sterols are extracted by placing 5 g of lyophilized callus tissue in 100 mL methanol and sonicated by treating with continuous, low power ultrasound for 30 min (Sonicator™, Heat Systems-Ultrasound, Inc.). The extraction procedure is performed in darkness under constant temperature of 25° C. The resulting extract is evaporated to dryness using a rotary evaporator. The resulting residue is then weighed, and 50 mg of the sample is cold saponified by shaking the sample constantly for 24 hours at room temperature (25° C.) with 5 mL of 1 M methanolic-KOH. The solution is then extracted three times with 2 mL hexane and 0.2 mL ethanol. The hexane fraction is dried under nitrogen and the unsaponifiable fraction is silanized at room temperature with a 2-mL mixture containing pyridine/hexamethlydisilazine/trimethylchlorosilane (5:2:1). After 1 one hour incubation, the liquid is evaporated under nitrogen in an 80° C. water bath then extracted three times with 0.3 mL hexane. The resulting organic fractions are combined and centrifuged and the resulting supernatant is used directly for GC analysis. One microliter of this sample is injected into an Agilent 6890 GC containing a DB-5MS column (30 m×0.25 mm×0.25 µm) with flame ionization detection using an Agilent 7360 autosampler system. Chromatographic separation is obtained by running an oven temperature program that heats from 220° C. to 300° C. at 5° C. per min with injector and detector temperatures set at 300° C. and 350° C., respectively. The proportions of the major sterol peaks are estimated by generating concentration curves using available standards and comparing profiles of wild-type and mutant callus extracts to these. While we can quantify known steroid components using these methods, the possibility of enhanced GFP fluorescence and displacement activity being due to the accumulation of other, perhaps uncharacterized, metabolites makes the examination of these profiles crucial. For example, if extracts from mutant tissue displaying reproducible displacement activity fail to show any quantitative differences in major peaks compared to wild-type extracts, the chromatographic data will need to be carefully scrutinized for the presence of new peaks, or minor peaks that are of greater abundance in mutant extracts. These previously absent or trace-level peaks will then be examined as thoroughly as possible by GC-MS analysis. This will be performed on an Agilent 6890 GC system coupled to an Agilent 5973 mass-selective detector. The conditions used are identical to those described for GC-FID analysis, with the following modifications. The mass spectra are recorded between 40 and 600 amu with an electron energy of 70 eV. The injector temperature and ion source temperature are set at 300° C. Qualitative analysis is based upon comparison of retention times and spectra with corresponding data logged in the Wiley Library mass spectral database.

Example 7

Genomic Cloning Techniques (Plasmid Rescue, Genomic Walking) to Recover Genomic DNA Adjacent to the Activation T-DNA Tags from the Individual Lines The most straightforward and efficient technique for cloning plant genomic DNA flanking the T-DNA insertion site is plasmid rescue. This approach relies on the bacterial origin of replication and the ampicillin antibiotic resistance gene encoded within the plasmid that is incorporated into the activation-tag T-DNA element (Walden et al. 1995; Weigel et al. 2000; incorporated herein). This method is applied after first examining the nature of the insert in a given mutant line by Southern blot analysis. Genomic DNA is isolated from young plant or callus tissue, whichever is the most abundant or available, and Southern analysis is conducted by probing with fragments of specific sequences within the T-DNA. A kanamycin resistance gene sequence and a second probe containing sequences within the bacterial plasmid located within the activation T-DNA are typically used. Screen-positive plant or callus genomic DNA digested with restriction endonucleases that do not cut within the T-DNA element (e.g., EcoRI and NotI) is used in a first analysis. Hybridization patterns indicating single insertions and sizes greater than that of the 5.7-kb T-DNA, are candidates for plasmid rescue. We have had success in performing plasmid rescue using genomic DNA of the proper size range eluted directly from nucleic acid grade agarose gels as well as using total genomic DNA without prior electrophoretic separation. After purification and concentration of the digested DNA, plasmid rescue is conducted by ligating the digested genomic DNA en masse to recircularize all of the digested fragments and transforming these by electrporation (BioRad Gene Pulser) into a recombination-deficient *E. coli* strain (SURE® cells, Stratagene) to prevent rearrangements due to the presence of the multimerized enhancers (Weigel et al. 2000). Plasmids isolated from the resulting ampicillin-resistant colonies are then examined using standard methods and DNA sequencing. There are also restriction enzyme sites that can be employed to rescue sequences to the right or left half of the T-DNA. That is, there are sites located on either side of the integrated plasmid sequences within the T-DNA that can be used to recover genomic DNA only from one side of the T-DNA (Walden et al. 1995; Weigel et al. 2000). These various cloning options usually will permit the isolation of at least some clones containing several kb of genomic DNA. In cases where these approaches do not lead to a sufficient amount of recovered DNA, even a few hundred base pairs can be used to probe genomic libraries to obtain larger, contiguous fragments. In addition, because it is possible to elute specific size fractions from agarose gels and there is an efficient means to functionally test DNA by uptake into transgenic cells, rescued T-DNA tags associated with more than one locus can be tested by independently recovering genomic DNA in separate procedures, and then test these individually-derived clones for activity.

Example 8

Confirmation of Gene Function by Re-Incorporation of Isolated DNA into Protoplasts from the Original Transgenic Line The ultimate confirmation that the recovered tagged gene is responsible for the small-molecule phenotype is by functional analysis of the rescued DNA. Genomic DNA clones that are associated with the CaMV 35S promoter enhancers are used. Genomic fragments that are not directly associated with the enhancers, for example are derived from the left half of the T-DNA, which do not contain the enhancer sequences, or are isolated from genomic libraries, are incorporated into vectors containing the enhancers to cause the activation of any genes present. Such vectors have been constructed by Weigel and others, which have multiple cloning sites within a T-DNA element containing the 35S enhancers and a plant selectable marker (Weigel et al. 2000) and can be used herein. The fastest means of conducting this functional test with such cloned plant DNA is by transient expression analysis after polyethylene glycol (PEG)-mediated DNA uptake (Walden et al. 1995). This method is carried out with freshly prepared protoplasts from leaves of the same NRP transgenic plants used for the mutagenesis and screening, which contain the hormone receptor based detection system. DNA uptake into protoplasts is performed by first preparing the isolated plant cells by washing in W5 media in standard polystyrene centrifuge tubes, and resuspending in a solution containing 450 mM mannitol, 15 mM $MgCl_2$, 0.1% MES (pH 5.6) to a final concentration of $1\times10^6$ protoplasts per mL. This is used to prepare 300 μL aliquots of the protoplast suspension, which are heat shocked at 45° C. for five minutes followed by cooling on ice for two minutes. At room temperature, 10 μL of a DNA sample is added at 1 μg μ$L^{-1}$, and incubated for ten minutes. At this point a PEG-containing solution consisting of 0.1 M $Ca(NO_3)_2 \cdot 4H_2O$, 0.4 M mannitol, 40% PEG 3350 (Sigma) (pH 7-9), is added and mixed to the cells and DNA and incubated 20 minutes at room temperature. After this incubation, 4.4 mL of 0.4 M sucrose-K3 growth media, containing required growth factors (NAA 1 μg μ$L^{-1}$, 0.2 μg μ$L^{-1}$ kinetin) is added. The protoplasts are then transferred to 60-mm petri dishes, sealed with parafilm and incubated at 26° C. in the dark for two days. After this time the protoplasts are placed in the light (20 μE $m^{-2}$ $s^{-1}$) in an incubator also at 26° C. Examination for GFP fluorescence can occur at this stage and can be monitored over the next several days. Appropriate controls, including plasmids containing enhancer sequences but no genomic DNA are included. After five days, cells can be embedded into agarose, as conducted with *Agrobacterium*-transformed cells, to enable continued growth under selective conditions, but we have found that for examining the effect of the inserted DNAs in larger, callus tissue, it is more efficient to proceed with standard *Agrobacerium*-mediated transformation into whole tobacco leaves based on the "leaf dip" transformation protocol. This gives stably transformed callus faster than waiting for the single cells from DNA uptake to grow into microcalli. Moreover, for DNA uptake into protoplasts, expression is transient, and it may be necessary to evaluate the effect of the transferred sequences in the larger, stably expressed callus format. Another factor is the fact that this tissue is also the type on which the primary screen is conducted. However, the activity screen is simply by examination under blue-wavelength light and thus can also be monitored continuously and at very early stages.

Example 9

Determination of All Genomic DNA Sequence Isolated by High Throughput DNA Sequencing The complete nucleotide sequence of all rescued or otherwise recovered genomic DNA associated with the T-DNA tags may be obtained. A given genomic clone may not necessarily be contiguous, as separate methods may be employed to recover a sufficiently sized portions of DNA, such as two-stages of plasmid rescue, or genomic screening approaches, as described in Objective 5, but these will all be assembled to provide a fully sequenced genomic fragment for analysis. Elucidation of the complete sequence will only be conducted on clones examined for proper restriction digest patterns and, where necessary, additional analysis by PCR, particularly for regions close to the T-DNA borders, where there can be incomplete transfer mainly at the 5' end, or the introduction of extra DNA. For example, sequences derived from the *Agrobacterium* binary vector "backbone" can be transferred into the genome in addition to the T-DNA, and can obscure the precise insertion point into the genomic DNA.

The basic strategy to be followed will be to mechanically shear each recovered clone using a "HydroShear®" (GeneMachines, San Carlos, Calif.) high pressure shearing device into random fragments centered at 1.8-kb, and cloning these into suitable, blunt-end digested and phosphatase-treated vectors (Oefner et al. 1996). Colonies harboring recombinant plasmids after transformation with ligated mixtures of clones will be automatically gridded to hybridization membranes and probed with sequences from within the activation-tagging element (e.g., the hygromycin resistance gene, 35S CaMV enhancer sequences) to identify clones containing T-DNA. Recombinant clones showing the absence of the main portion of the T-DNA are sequenced.

All output from the ABI automated DNA sequencers is fully readable using LaserGene (DNASTAR, Madison, Wis.) sequence analysis software consisting of SeqMan, EditSeq, and MegAlign programs, among others. This and the related packages of DNA analysis programs have been in use in our laboratories for the past several years and therefore all of the respective laboratory members have experience with the programs. These programs are used extensively to compile, assemble and analyze sequences, including providing direct formats to the National databases.

Example 10

Further Characterization of Genes in Regenerated Mutant Plants to Establish Whether the Gene Influences Product Synthesis at this Level As noted in Example 4, early in the process to confirm any fluorescing mutated callus clone, available material is transferred to shoot-inducing media (MS media plus 0.10 mg L−1 NAA 0.5 mg L−1 benzylaminopurine). In addition, genetic material introduced into the NRP-based detector lines during the evaluation of isolated genomic sequences provides new stably transformed lines that can be evaluated for GFP fluorescence throughout their development into whole plants. This provides two important levels of analysis for the sequences that are identified. One is the examination of lines derived independently that overexpress genes associated with an enhancer, and the other are lines derived from the original, GFP-positive, microcallus clones.

Example 11

Screening Using the Human Estrogen Detector System in *Arabidopsis*

Putative mutants that accumulate phytoestrogens have been identified by screening mutagenized populations of a transgenic *Arabidopsis* line harboring a human nuclear receptor system. The primary genetic screen was conducted by examining young seedling roots for expression of the green fluorescent protein by fluorescence microscopy. Out of approximately 8,000 lines screened, a subpopulation of about 49 lines were scored as putative positive on this basis and used to generate progeny to perform a secondary screen. A portion of this population has been examined and some (4-5) individuals exhibited GFP expression as detected by visual inspection. Whole-seedling extracts were prepared from this first group and used to determine phytoestrogen "activity". Analysis by estrogen binding displacement assays indicated that elevated levels of β-estradiol-equivalent activities were detected in two lines compared to a negative control, as indicated in Table I.

TABLE I

Binding Activity in Putative (GFP expression-positive) Lines

| | Line: | | |
|---|---|---|---|
| | 4 | 5 | Neg. control |
| Approx. Activity* (nM) | 30 | 10 | 0.01 |

*Activity expressed as β-estradiol activity equivalents

Thus, use of a mammalian nuclear receptor in transgenic plants demonstrates the versatility of the invention for screening mutagenized populations of seedlings or plant cells by the direct detection of biologically active metabolites.

What is claimed is:

1. A high throughput screening method for identifying plant cells that are the source of compounds that interact with a mammalian estrogen receptor ligand binding domain comprising, (1) transforming an *Arabidopsis* or *Nicotiana tabacum* plant with a vector having an estrogen receptor system comprising a constitutive promoter operably linked to a nucleotide sequence encoding a trimeric transcription factor comprising as operatively linked components a mammalian estrogen receptor ligand binding domain, a transcription factor DNA binding domain and a transactivating transcriptional activator domain; and a gene encoding a visible marker operably linked to a transcription activator sequence and a promoter, to obtain a transgenic plant;

(2) isolating protoplasts from the transgenic plant of step 1 that express the estrogen receptor system and the gene encoding the visible marker;

(3) mutagenizing the protoplasts of step 2 via T-DNA tagging mutagenesis to form mutagenized protoplasts;

(4) culturing the mutagenized protoplasts of step 3 into microcalli; and (5) selecting microcalli of step 4 that overexpress the visible marker gene in comparison to a control transgenic microcallus.

2. The method of claim 1 further comprising
(a) preparing an extract of cells removed from a microcallus that overexpresses the visible marker gene, wherein removal of the cells does not destroy the microcallus;
(b) testing the extract of step (a) for the presence of small molecules and/or compounds that bind to the estrogen receptor ligand binding domain.

3. The method of claim 2 further comprising recovering genomic DNA adjacent to and within about 5.7 kb of an activation T-DNA tag in protoplasts or callus tissue that contain small molecules or compounds that activate the estrogen receptor ligand binding domain.

4. The method of claim 3 further comprising cloning the genomic DNA that is recovered into a second vector comprising enhancer sequences such that the enhancer sequences are operably linked to the genomic DNA; transforming protoplasts isolated from plants transformed with the vector of step (1) with the second vector; and monitoring the protoplasts for expression of the visible marker gene.

5. The method of claim 1 wherein the plant is a tobacco plant.

6. The method of claim 1 wherein the plant is *Arabidopsis*.

7. The method of claim 1 wherein the visible marker gene encodes green fluorescent protein.

8. The method of claim 2 wherein the binding of the small molecule or compound results in activation of the estrogen receptor.

9. The method of claim 2 wherein binding to the mammalian estrogen receptor is detected in plant cells or tissues by the corresponding activation of a visible marker gene.

10. The method of claim 2 wherein confirmation of small molecule activity is by a radioligand displacement assay.

11. The method of claim 1 wherein the mutagenized protoplasts are exposed to an inducer of the estrogen receptor ligand binding domain.

12. The method of claim 11 wherein the inducer is β-estradiol.

13. A high throughput screening method for identifying cells that are the source of plant small molecules or compounds capable of activating a mammalian estrogen receptor protein comprising, (1) transforming an *Arabidopsis* or a *N tabacum* plant with a vector comprising a constitutive promoter operably linked to a nucleotide sequence encoding a trimeric transcription factor comprising as operatively linked components a human estrogen receptor hormone binding domains, a yeast GAL4-DNA binding domain and a transactivating herpes simplex V16 transcriptional activator domain; and a gene encoding a visible marker operably linked to a transcription activator sequence and a promoter, to obtain a transgenic plant;

(2) isolating protoplasts from the transgenic plant of step 1 that express the gene encoding the visible marker;

(3) mutagenizing the protoplasts of step 2 via T-DNA tagging mutagenesis to form mutagenized protoplasts;

(4) culturing the mutagenized protoplasts of step 3 into microcalli; and (5) selecting microcalli of step 4 that overexpress the visible marker gene in comparison to a control transgenic microcallus.

14. The screening method of claim 13 wherein the constitutive promoter of the vector is the 35S promoter of the cauliflower Mosaic Virus (CaMV).

* * * * *